United States Patent

Byer

[11] Patent Number: 5,310,341
[45] Date of Patent: May 10, 1994

[54] DENTAL APPARATUS
[76] Inventor: Joseph I. Byer, 36601 Howard Rd., Farmington Hills, Mich. 48331
[21] Appl. No.: 3,315
[22] Filed: Jan. 12, 1993
[51] Int. Cl.⁵ ............................ A61C 1/16; A61C 3/02
[52] U.S. Cl. ...................................... 433/116; 433/165
[58] Field of Search ................................. 433/116, 165
[56] References Cited

U.S. PATENT DOCUMENTS

| | | | |
|---|---|---|---|
| 1,549,165 | 8/1925 | Thiedemann | 433/116 |
| 1,636,577 | 7/1927 | Schuller | 433/165 |
| 3,324,552 | 6/1967 | Saffir | 433/116 X |
| 4,424,036 | 1/1984 | Lokken | 433/116 |
| 4,526,542 | 7/1985 | Kochis | 433/165 |
| 4,967,320 | 10/1990 | Paschal | 362/96 |
| 5,197,876 | 3/1993 | Coston | 433/116 |

FOREIGN PATENT DOCUMENTS 181358  3/1955  Fed. Rep. of Germany ...... 433/116
1002502 2/1957 Fed. Rep. of Germany ...... 433/116

Primary Examiner—Gene Mancene
Assistant Examiner—Cindy A. Cherichetti
Attorney, Agent, or Firm—Jerry G. Beck

[57] ABSTRACT

A dental apparatus, in combination with a dental handpiece that incorporates a rotable chucking mechanism with a locking means, and a driving mechanism that rotates the chucking mechanism at high speeds when actuated, comprising a dental bur which has a tool head at one end and a shank segment at the other end, a portion of the shank segment is received and locked in the chucking mechanism, and a barrier and deflecting means mounted intermediate the ends of the dental bur, the barrier and deflecting means upon being rotated by the chucking mechanism forming a barrier or shield and also creating air streams to intercept and prevent airborne particles generated by dental procedures from being deposited on and in the handpiece.

12 Claims, 2 Drawing Sheets

DENTAL APPARATUS

BACKGROUND OF THE INVENTION

1. Field of Invention

The present invention relates to a dental apparatus that is incorporated in dental burs or tool bits mounted in a handpiece held by a dentist or dental technician to prevent or at least minimize such matters as blood aerosols, saliva, dental debris and the like generated during dental operations to be deposited on or within any part of the handpiece. The dental apparatus of this invention installed on dental burs provide for a barrier and deflecting means which, upon the high speed rotation of the dental bur, will prevent air-borne foreign matter from approaching or contacting the handpiece held in the hands of the dentist or dental technician.

2. Description of Related Art

With the recent spread of Aids (acquired immune defiency syndrome), new exacting procedures are being developed and utilized to minimize the transfer of infectious matter to the dentist, dental technicians, and dental patients. Further, other various pathogens, both blood-borne or saliva-borne, can be present in the dental work area. One procedure calls for steam autoclaving or chemi-claving the handpiece utilized after each use. Even, if such procedure is followed, there is still a probability that some infectious matter is not completely destroyed by the sterilization method. Although so far, little evidence has been uncovered in scientific circles to support that the possibility of contraction of Aids or other infectious diseases from patients by dental personnel through the spray of infected matter or particles, it is only proper to provide as many safeguards as possible to reduce the the contamination of tools such as the handpiece of the dental unit used by the dentist during the treatment of patients.

The prior art has recognized the need for eliminating or reducing the exposure to dental personnel to infectious foreign matter propelled from the patient's mouth during dental operations.

In U.S. Pat. No. 4,967,320, an apparatus is disclosed which utilizes an air screen to form a protective envelope about the patient's head to serve as a barrier against air-borne particles. These particles are transported by the air stream downward after being intercepted to a disposable patient drape. This prior art apparatus, although it recognizes the problem, is very cumbersome as the formed envelope is maintained in a fixed position but it can be easily disturbed by the movement of the dentist or his technician.

In U.S. Pat. No. 1,549,165, a protector cap for the dental handpiece has been devised to prevent the entry of foreign matter into the handpiece and the escape of oil from the handpiece mechanism. In this patent, a cap is inserted over the tool and tool holder and directly secured to the handpiece by a spring gripping device. The cap acts as a seal to prevent entry of foreign matter but does not deflect foreign infectious matter or minimize their deposition on the handpiece itself or on the fingers of the dental technician holding the handpiece.

The Applicant has developed a simple low-cost device comprising a barrier and deflecting means which is either attached to or integrally formed with the shank segment of a conventional dental bur or tool bit that is normally inserted by the dental technician into the chucking mechanism of the regular handpiece. The barrier and deflecting means of this invention consists of a bushing with or without a flange extending outwardly therefrom that fits tightly over the shank segment of a conventional dental bur or it could be integrally formed with the shank. Attached to the bushing or flange are a plurality of blades that extend outwardly from the bushing or downwardly from the flange. These blades are twisted so as to provide a down draft upon being rotated at high speed. The barrier and deflection means, upon insertion of the bur in the chucking mechanism of the handpiece, will be positioned just below the bottom edge of the handpiece and well above the tool head of the bur so as to not interfere with the dental operation or mechanisms. The high speed rotation of the dental bur upon actuation of the handpiece mechanism by the dentist or technician, will result in the barrier and deflecting means to form an invisible shield to serve as a barrier to prevent the entry of air-borne matter into openings in the bottom portion of the handpiece. Further, the rotation of the blades will create a downdraft to deflect air-borne particles and matter to prevent their deposition onto the surface of the handpiece as well on the fingers of the dentist or dental technician.

The barrier and deflecting means of this invention incorporated in the dental bur can be made to be disposable as the device is readily removable from the dental bur with a conventional tool and then easily replaced with a new device at a very low cost. It can also be sterilized together with the dental bur if it is not removed or integrally formed therewith. The utilization of the device of this invention may allow for the less frequent sterilization of the close tolerance designed handpiece which should result in reduced service problems as frequent sterilization has a major impact on the life and operation of the handpiece.

SUMMARY OF THE INVENTION

In the present invention, a barrier and deflecting means has been developed which is either pressfitted on the shank segment of a standard dental bur or is integrally formed therewith. The barrier and deflecting means is provided with a bushing having a bored hole in its center. The bored hole receives the shank segment of the dental bur. The diameter of the hole is selected to assure that a pressfit is achieved about or near the middle of the bur so that when the end portion of the shank segment is received in the chucking mechanism of the handpiece, the barrier and deflecting means will remain clear of the bottom of the handpiece. Blades extending from the bushing or flange are angled or twisted similar to a propeller to create an airstream like a fan in a generally downward and/or radial direction. The blades provided can range from at least one to a plurality of blades. In the preferred embodiment of this invention, the blades extend downward from a flange that is integrally formed with the bushing although the blades could be horizontally or diagonally disposed as long as the interference with the handpiece functions are minimized. The airstream created by the blades upon the high rotation of the bur will deflect airborne particles including saliva and blood aerosols or dental debris generated by the application of the dental burs to the teeth or gums of the patient by the manipulation of the handpiece by the dentist. Those airborne particles not deflected by the airstream are prevented from entering the openings in the bottom of the handpiece by the rotating blades and flange or bushing which form a barrier which, at the high rotational speed, is invisible to the eye but becomes an effective shield.

The barrier and deflecting means is quite effective in keeping airborn foreign matter from being deposited on the handpiece. The barrier and deflecting means does not have to come into contact with the dentist or dental technician as it is removed upon release of the dental bur from the chucking mechanism and then, it is either disposed of or dropped directly into a sterilization tray.

The primary objective of this invention is to provide a relatively low cost device directed at preventing, or at least minimizing, the exposure of the dental handpiece held by the dentist or dental technician to foreign matter propelled from the patient's mouth during dental operations.

A further objective is to increase the longevity of the handpiece by allowing for a potential reduction in the cleaning and sterilization cycles of the handpiece.

These and other objectives will become more apparent with reference to the accompanying drawings and the following specification.

DESCRIPTION OF THE PREFERRED EMBODIMENT

Figure 1:
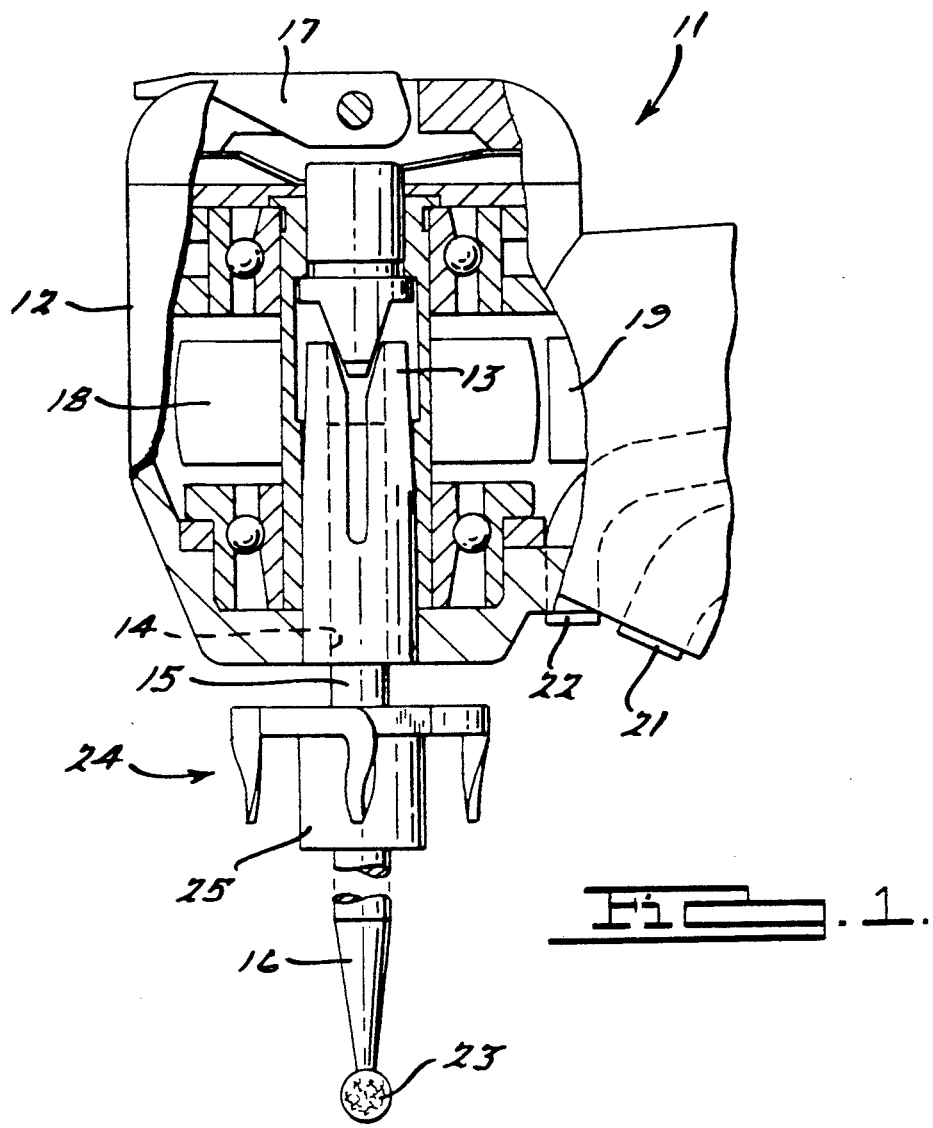
FIG. 1 is a cut-away view depicting the interior of a head of a handpiece supporting a dental bur incorporating the device of the preferred embodiment of this invention.

In FIG. 1 is shown a conventional dental handpiece 11 with the front wall cut away to show its interior mechanism which is not part of this invention. The handpiece 11 comprises a head 12 which contains a chucking mechanism 13 or collet provided with a center bore 14. This center bore 14 receives the end portion of a shank segment 15 of a dental bur 16 or tool bit. The chucking mechanism 13 illustrated in FIG. 1 features a locking and release lever 17 to lock in the shank segment 15 of the bur 16 when the locking and release lever 17 is in the position as shown. To release the dental bur 16, the lever 17 is pivoted in an upward direction which opens up the bore 14 to allow the dental bur 16 to fall out of the chucking mechanism 13. The chucking mechanism 13 is driven at a high rotational speed by a turbine motor 18 which is energized by pressurized air transmitted through a flexible tube 19 from an air pressure source (not shown). The turbine motor 18 is actuated by a conventional switching device (also not shown) manipulated by the dentist or dental technician. A liquid cooling conduit 21 is provided that terminates at the bottom of the handpiece 11 adjacent to the chucking mechanism 13 to bring coolant to the dental bur 16 when actuated by the dentist or technician holding the hand piece 11. At times, a light emitting source 22 is also positioned within the head 12 to light up the dental work area in the mouth of the patient.

The dental bur 16 has the shank segment 15 extending from one end thereof to the other end where it is provided with a tool head 23 that can either be a drill, grinding wheel, a burr, a reamer, or any other tool function selected by the dentist or the technician to undertake the required procedures in the mouth of the patient. A portion of the shank segment 15 at one end of the bur 16 is received in the center bore 14 of the chucking mechanism 13 and locked in place by the lever 17 as seen in FIG. 1.

The dental bur 16 of this invention is provided with a barrier and deflecting means 24 which is either integrally formed with the shank segment 15 intermediate its ends or it can be mounted onto the shank segment 15 so that it fits tightly around the diameter of the shank segment 15 near the center thereof. The barrier and deflecting means 24 has to be positioned on the shank segment 15 so that when a portion of the shank segment 15 is received in the bore 14 of the chucking mechanism 13, sufficient clearance between the bottom edge of the handpiece 11 and the barrier and deflecting means 24 is maintained to eliminate any interference between the rotating bur 16 and the stationery handpiece 11 as seen in FIG. 1.

Figures 2, 3:
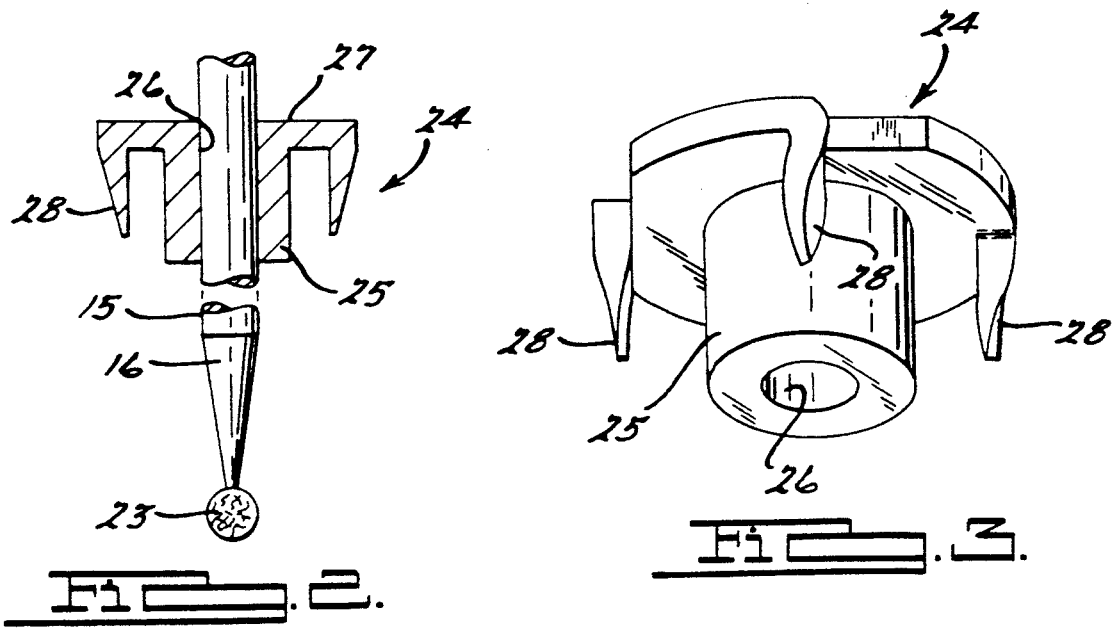
FIG. 2 is a an enlarged elevational sectional view of the device of this invention shown in FIG. 1.
FIG. 3 is a perspective view of the barrier and deflecting means of the device shown in FIG. 2.

In a preferred embodiment shown in FIG. 1, 2, and 3, the barrier and deflecting means 24 comprises a bushing 25, generally cylindrically shaped, with an axially bored hole 26. The bored hole 26 of the bushing 25 can be placed on the shank segment 15 of the bur 16 and pushed downward until it pressfits tightly on the shank segment 15 intermediate its ends. It could also be locked in place on the shank segment 15 mechanically or by an adhesive as alternatives. A circular flange 27 extends outwardly from the upper periphery of the bushing 25. At the outer edge of the flange 27, a plurality of blades 28 or teeth extend downwardly in the general direction of the tool head 23. The blades 28 are slightly rotationally twisted so as to create a downdraft away from the handpiece 11. In this embodiment, the blades 28 are formed by bending portions of the edge of the flange 27 downward and slightly twisting them to provide the directional air stream when the barrier and deflecting means 24 is rotated together with the bur 16 at high speeds.

In FIGS. 1-3, four blades 28 are shown extending from the periphery of the flange 27 but any number of blades can be utilized in the device of this invention to provide an adequate deflecting air stream. The flange 27 serves as a barrier or shield to prevent any airborne particles which may not have been deflected from depositing on the bottom edge of the handpiece 11 or enter any openings in the head 12 of the handpiece 11.

Figure 4:
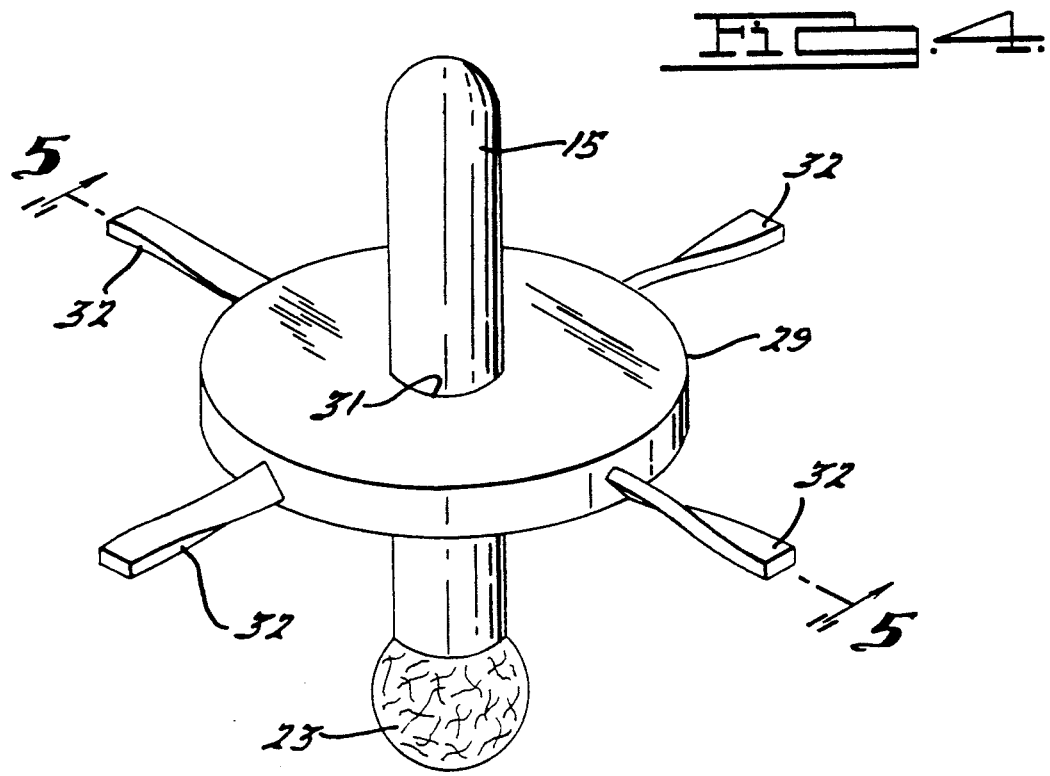
FIG. 4 is a perspective view of another embodiment of this invention.
Figure 5:
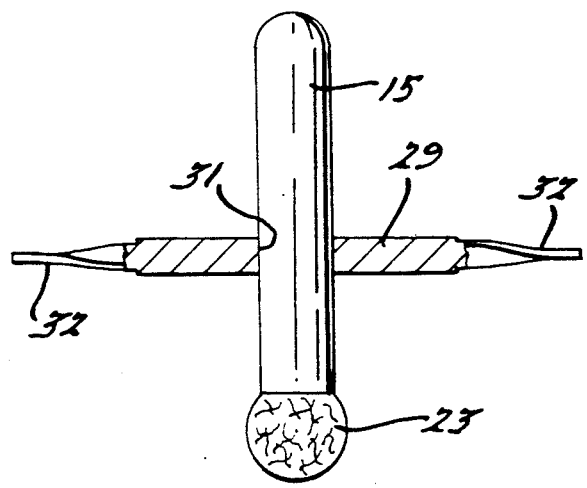
FIG. 5 is an elevational sectional view of the device shown in in FIG. 4 taken along line 5—5.

In FIGS. 4 and 5 is shown an additional embodiment of the barrier and deflection means 24 of this invention comprising a wider bushing 29 provided with an axially bored hole 31 which fits tightly on the shank segment 15 of the bur 16 to achieve a press-fit. Blades 32 extend in a generally horizontal outward direction from the periphery of the bushing 29. These blades 32 are slightly twisted to assume the shape of propellers. One blade 32 may be sufficient to create a downdraft but in the example shown in FIG. 5, four blades 32 are depicted. Any plurality of blades 32 are satisfactory but the inherent small size of the barrier and deflecting means 24 limit the number of blades 32 that can be employed. When rotated at high speeds, the blades 32 form a shield or barrier besides creating an air stream to prevent or minimize the deposition of foreign air-borne matter on or in the handpiece 11. The outer peripheral edge of the blades 32 is limited so as not to interfere with either the coolant or the lighting provided in the head 12 of the handpiece 11 to facilitate the dental procedures.

Figure 6:
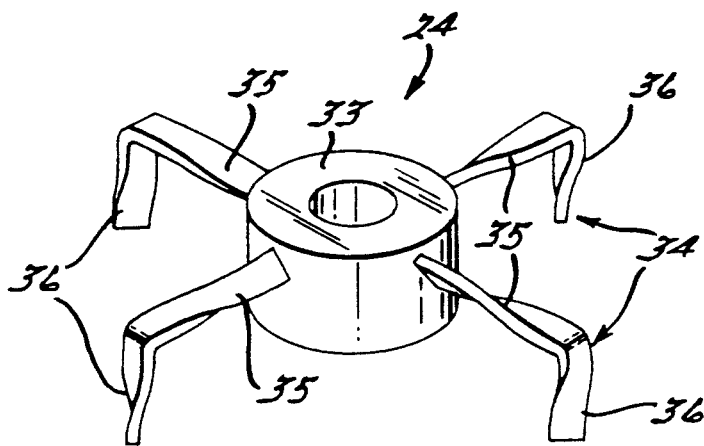
FIG. 6 is a perspective view of a further embodiment of this invention.

A further embodiment of this invention is shown in FIG. 6. In this embodiment, a cylindrical bushing 33 is provided from which a plurality of two-directionally blades 34 extend outwardly. Each blade 34 has a horizontally extending blade portion 35 and a vertically extending blade portion 36. The vertically extending blade portion 36 is joined to the blade portion 35 at the tip thereof and extends in downward direction parallel to the axis of the bushing 33. The horizontally extending blade portion 35 has a slight rotational twist to bring about a downward air stream similar to fan blades while the vertically extending blade portion 35 is also slightly twisted to provide an outward air stream away from the bushing 33. The horizontally extending blade portion 35 and the vertically extending blade portion 36 could be formed from one integral piece of material that is readily bendable.

This embodiment has the additional advantage of providing an air curtain that will intercept air-borne particles flying in horizontal as well in vertical directions in the immediate vicinity of the dental bur 16 to deflect them away from the handpiece 11.

It can be understood from the description of the embodiments of this invention that an effective, low cost device has been achieved which will reduce the potential contamination of the dental handpiece 11 by air-borne particles, which may include infectious matter, by mounting a barrier and deflecting means 24 directly on the dental bur 16, usually before it is inserted into the chucking mechanism 13 of the handpiece 11. The barrier and deflecting means 24 not only provides a shield or barrier to prevent the deposition of air-borne particles on or in the handpiece 11 but also sets up single or multiple continuous air streams when the dental bur 16 is rotated at high speeds to deflect the particles away from the handpiece 11. The barrier and deflection means 24 incorporated in this invention can be manufactured from a rigid or semi-rigid plastic or in some instances, could be made from a light weight, thin metal depending on the design. The barrier and deflection means 24 is readily mounted on the shank segment 15 of the dental bur 16 by the dentist or his/her assistant or it can be assembled or integrally formed with the shank segment 15 at the time of its manufacture. It can made disposable by having it made easily removable from the dental bur 16 by some special tool which would break the bond between the bushings 25, 29, and 33 and the shank segment 15. If integrally formed or not readily removable from the dental bur 16, the bur 16 together with the barrier and deflecting means 24 can be placed in sterilization equipment before being used again.

While only the preferred embodiments of the present invention have been described, others may be possible without departing from the scoped of the appended claims.

I claim:

1. A dental apparatus in combination with a dental handpiece having a head, said head encompassing a rotatable chucking mechanism with a locking means and actuatable driving mechanism, said driving mechanism rotating said chucking mechanism at high speeds upon being actuated, comprising a dental bur having a tool head at one end and a shank segment at the other end, a portion of said shank segment being received in said chucking mechanism, said locking means locking said portion of said shank segment in said chucking mechanism, and a deflecting means mounted on said shank segment intermediate said portion of said shank segment received in said chucking mechanism and said tool head of said dental bur, said deflecting means upon being rotated at high speeds by said chucking mechanism when actuated by said driving mechanism forming an invisible barrier and shaped to create at least one continuous air stream to deflect air-borne particles away from said head to prevent deposition of said particles on and in said dental handpiece.

2. A dental bur used in conjunction with a dental handpiece, said dental handpiece incorporating a chucking mechanism and a driving mechanism to rotate said chucking mechanism at high speeds, said dental bur comprising a tool head at one end and a shank segment having an end portion at the other end, said end portion being received in said chucking mechanism, and a deflecting means mounted on said shank segment intermediate the end portion of said shank segment and said tool head of said dental bur, said deflecting means upon being rotated by said chucking mechanism shaped to create at least one continuous air stream to deflect air-borne particles away from said dental handpiece to prevent the deposition of said air-borne particles on and in said handpiece.

3. A dental bur as defined in claim 2 wherein said deflecting means comprises a plurality of blades that extend in a general outward direction from said shank segment.

4. A dental bur as defined in claim 2 wherein said deflecting means comprises a cylindrical bushing having a hole, said shank segment being received tightly in said hole, a flange extending radically outwardly from said bushing, and at least one blade extending from the periphery of said flange, said blade being slightly twisted to create a directional air stream away from said dental handpiece upon being rotated.

5. A dental bur as defined in claim 2 wherein said deflection means comprises a cylindrical bushing having a hole, said shank segment being received in said hole, a locking means to lock said bushing to said shank segment, and at least one blade extending from the periphery of said bushing, said blade creating air streams upon rotation of said dental bur.

6. A dental bur as defined in claim 5 wherein said blade is rotationally twisted to provide an air stream in the direction of said tool head and away from said handpiece.

7. A dental bur as defined in claim 5 wherein said blade comprises a horizontally extending blade portion and a vertically extending blade portion, said horizontally extending blade portion creating an air stream in a downward direction and said vertically extending blade portion creating an air stream in a radial outward direction.

8. A dental bur as defined in claim 7 wherein said vertically extending blade portion extends in a downward direction from the outer tip of the horizontally extending blade portion substantially parallel with the axis of said hole.

9. A dental bur as defined in claim 5 wherein said blade is propeller shaped.

10. A dental bur as defined in claim 5 wherein said means locking said bushing to said shank segment can be unlocked to allow for the removal of said deflection means from said dental bur.

11. A dental bur as defined in claim 2 wherein said deflecting means is made from a disposable plastic material.

12. A dental bur as defined in claim 2 wherein said deflection means comprises a plurality of blades, said blades having blade portions disposed in different planes to create air streams in multi-directions upon being rotated.

* * * * *